United States Patent
Cai et al.

(10) Patent No.: US 8,940,685 B2
(45) Date of Patent: Jan. 27, 2015

(54) METHOD FOR PREPARING ACTIVE PEPTIDES FROM CORN GERM PROTEINS

(71) Applicant: China National Research Institute of Food and Fermentation Industries, Beijing (CN)

(72) Inventors: Muyi Cai, Beijing (CN); Ruizeng Gu, Beijing (CN); Weixue Yi, Beijing (CN); Jun Lu, Beijing (CN); Yong Ma, Beijing (CN); Zhe Dong, Beijing (CN); Yaguang Xu, Beijing (CN); Xingchang Pan, Beijing (CN); Yongqing Ma, Beijing (CN); Feng Lin, Beijing (CN); Zhentao Jin, Beijing (CN); Liang Chen, Beijing (CN); Lu Lu, Beijing (CN); Wenying Liu, Beijing (CN)

(73) Assignee: China National Research Institute of Food and Fermentation Industries, Beijing (CN)

( * ) Notice: Subject to any disclaimer, the term of this patent is extended or adjusted under 35 U.S.C. 154(b) by 0 days.

(21) Appl. No.: 13/894,379

(22) Filed: May 14, 2013

(65) Prior Publication Data
US 2013/0252877 A1    Sep. 26, 2013

Related U.S. Application Data

(63) Continuation-in-part of application No. PCT/CN2011/000862, filed on May 17, 2011.

(51) Int. Cl.
  *C12P 21/06*   (2006.01)
  *A61K 36/899*   (2006.01)
  *A61K 36/88*   (2006.01)
  *C07K 14/415*   (2006.01)
  *C07K 5/062*   (2006.01)
  *A61K 38/01*   (2006.01)

(52) U.S. Cl.
  CPC .............. *C12P 21/06* (2013.01); *A61K 38/011* (2013.01); *C07K 5/06026* (2013.01); *A61K 36/899* (2013.01); *C07K 14/415* (2013.01)
  USPC ......... 514/1.1; 435/68.1; 514/15.6; 514/15.7; 514/16.3; 530/300; 530/343; 426/656

(58) Field of Classification Search
  CPC ......... A23L 1/172; A23L 1/3025; A23J 3/34; A23J 3/34; A23J 1/125; A23J 1/00; A23J 3/346; A23J 3/30; A23C 9/12; A23V 2200/326; A23V 2200/30; A23V 2200/00; A23V 2250/55; A23V 200/548; A23V 2200/54; A61K 38/011; A61K 38/16; A61K 36/899; A61K 36/88; A61K 38/01; A61K 38/02; C07K 1/36; C07K 14/415; C07K 14/425; C07K 5/06026; C12P 21/06
  See application file for complete search history.

(56) References Cited

FOREIGN PATENT DOCUMENTS

| | | |
|---|---|---|
| CA | 2 732 614 | 2/2010 |
| CN | 1526299 A | 9/2004 |
| CN | 1799395 A | 7/2006 |
| CN | 1800206 A | 7/2006 |
| CN | 1800207 A | 7/2006 |
| CN | 1935016 A | 3/2007 |
| CN | 101130801 A | 2/2008 |
| CN | 101514355 A | 8/2009 |
| CN | 101531700 A | 9/2009 |
| CN | 101798587 A | 8/2010 |
| CN | 101890151 A | 11/2010 |
| EP | 0 445 606 A1 | 9/1991 |
| JP | H06-087886 A | 3/1994 |
| JP | H07-502416 A | 3/1995 |
| JP | 2000-290292 A | 10/2000 |
| JP | 2001-233789 A | 8/2001 |
| JP | 2011-522210 A | 7/2011 |
| WO | 9312667 A1 | 7/1993 |
| WO | 2008145763 A1 | 12/2008 |

OTHER PUBLICATIONS

Parris et al, J. Agric. Food Chem. (2008) 56, 2620-2623.*
Moreau et al., J Am Oil Chem Soc (2009) 86, 469-474.*
Lin et al., Food Chemistry (Feb. 2011) 124, 801-807.*
Chen et al., Journal of Jilin Agricultural University (2008) 30(5), 750-752.*
Yang et al., J Agric. Food Chem. (2007) 55, 7891-7895.*
Boelsma etl al., British Journal of Nutrition (2009) 101, 776-786.*
Lin et al., Food Chemistry (2011) 124, 801-807.*

(Continued)

*Primary Examiner* — Karlheinz R Skowronek
*Assistant Examiner* — Catherine Mader
(74) *Attorney, Agent, or Firm* — J.C. Patents

(57) ABSTRACT

The present invention discloses a method for producing antihypertensive active peptides with corn germ protein as the material. The method comprises an alkali-heat treatment and continuous enzymolysis of the corn germ protein. The components with molecular weight less than 1000 Da in the active peptides obtained according to the present method account for more than 92%, and alanine-tyrosine (Ala-Tyr, AY) as the characteristic peptide fragments in the antihypertensive peptides accounts for more than 0.6%, so that the active peptides have a good ACE inhibitory activity in vitro as well as stability against temperature, pH and major gastrointestinal digestive enzymes, and have a significant effect of lowering blood pressure on spontaneous hypertension rats in vivo. The active peptides can be applied as a new functional nutrient to development and production of food, health food and pharmaceutical.

4 Claims, 3 Drawing Sheets

(56) References Cited

OTHER PUBLICATIONS

International Search Report of International Application No. PCT/CN2011/000862, dated Feb. 23, 2012.

Li, Zisheng et al., "Research of Techniques on Enzymatic Hydrolysis of Corn Protein Powder" Food and Fermentation Industries, 2006, vol. 32, No. 4, pp. 67-69.

Zheng, Yun et al., "Study on the Hydrolysis of Egg Albumin" Food and Fermentation Industries, 2005, vol. 31, No. 12, pp. 69-71.

Lin, Feng et al., "Study on the Hydrolysis of Corn Protein Isolate Based on the Response Surface Method" Food and Fermentation Industries, 2008, vol. 34, No. 1, pp. 60-64.

Zhang, Ming-Di et al., "Research of Ultrafiltration techniques on enzymatic hydrolysates of corn germ protein" Food Science and Technology, 2006, No. 3, pp. 37-40.

Chen, Yan-Ping et al., "Study on Hydrolysis of Corn Germ Protein with Aid of Papain" Journal of Jilin Agricultural University, 2008, No. 5, pp. 750-752.

\* cited by examiner

METHOD FOR PREPARING ACTIVE PEPTIDES FROM CORN GERM PROTEINS

CROSS-REFERENCE TO RELATED APPLICATIONS

This application is a continuation-in-part of, and claims the priority benefit of International Application No. PCT/CN2011/000862 filed on May 17, 2011 entitled Industrial production method for producing antihypertensive bioactive peptide, and U.S. patent application Ser. No. 13/781,264, entitled Method for preparing active peptides from corn germ proteins, filed on Feb. 28, 2013, both of which are hereby incorporated by reference in their entirety.

FIELD OF THE INVENTION

The present invention belongs to the biological technical field, and particularly relates to a method for preparing active peptides, with corn germ proteins as raw material. The obtained active peptides have an antihypertensive function, and can be applied to functional food and nutrition and health care products.

BACKGROUND

Bioactive peptides refer to the peptides compounds beneficial to life activity of organisms or having physiological effects, which are peptides fragments with smaller molecular weight obtained by enzyme digestion of macromolecules of proteins. Compared to proteins, the active peptides are small molecules but with high biological activities, and a small amount of peptides can play an extremely important and remarkable physiological role. Since Hughes et al first reported that small peptides with an activity similar to morphine were found in animal tissues in 1975, a variety of bioactive peptides have been isolated from animals, plants and micro-organisms. It has been proved by research that various bioactive peptides products obtained from natural protein enzymolysis can be easily absorbed by the human body, and the specific structures and properties of which generally exhibit a variety of physiological functions including anti-oxidation, anti-fatigue, lowering blood fat, lowering blood pressure, strengthening immunity and the like. Preparing bioactive peptides by enzymolysis of proteins from nature sources has the advantages of wide raw material sources, no toxic and side effects, capable of scale production, low price, etc. Therefore, in recent years the research and development of bioactive peptides have become a major development direction in the global food and nutrition-related research fields.

Hypertension is a disease seriously threatening to human health. The global *hypertension impact report* issued in 2007 gave warning that the number of people suffering from hypertension has an increasing trend in the world, and currently stands at 1 billion; if no effective measures were taken, by 2025, the world would have 1.56 billion people suffering from the disease. The number of hypertensive patients may increase by 80% in some countries, including China. Angiotensin I-converting enzyme (ACE) is a kind of multifunctional dipeptide carboxypeptidase, which can convert angiotensin I without physiological activity into angiotensin II with blood pressure rising effect, and can also degrade Bradykinin into inactivation fragments, which leads to vasoconstriction, and results in elevated blood pressure. Inhibiting ACE activity by ACE inhibitors to hinder the conversion of angiotensin I into angiotensin II has become the primary means of hypertension prevention.

According to disclosures in some reports, more than 30 kinds of synthetic ACE inhibitors have entered into clinical research or applications. Although these synthetic inhibitors have significant blood pressure-lowering effect, they can also cause many side effects, such as cough, allergy, rash, edema, cardiac arrhythmia and kidney damage, etc. Therefore, the demand for researching and developing safer and more effective ACE inhibitors are becoming more and more urgent.

With the rise of the "return to nature" philosophy and the biologically active peptides research, extracting safe, effective, no side-effect ACE inhibitory peptides from natural animal and plant resources has become a hot spot in the research of hypertension prevention. So far, the edible food-borne peptides put into industrial production have mostly been early researched soybean peptides, milk peptides, marine peptides, etc.

As one of the three major food crops, corn plays an important role in the world's food structure. Corn germ protein powders, as the main byproduct in the wetting process of corn starch, are rich in protein, also contain inorganic salts and a variety of vitamins and other ingredients, but they are underused. In China, for example, corn germ protein powders are mainly used for feed industry or are naturally discharged. Annual natural discharge of corn protein is up to 0.1 million tons, which not only is a waste of valuable food resources, but also causes serious pollution to environment.

Currently, there is little research on obtaining bioactive peptides from the corn germ protein powders. According to the present invention, the technology of protein enzymolysis is used to establish an industrialized method for obtaining corn antihypertensive active peptides from corn germ protein powders, and it has been proved that the obtained products have definite characteristic components and biological activity, which have great practical value and economic benefits to the full use of the rich resources of corn as well as to develop functional foods and nutrition health care products.

SUMMARY

The object of the present invention is to provide a method of preparing active peptides from corn germ proteins, to broaden the processing and utilization of corn germ protein, and meanwhile, to obtain corn active peptides with an antihypertensive function, and the method can be applied in industry production.

The present invention provides a method for preparing active peptides from corn germ protein powder, including the following steps:

adding the corn germ protein powders to a reaction tank, mixing the corn germ protein powders with water to form a first feed liquid, and the feed liquid being adjusted to be alkalescent, heated to 50~90° C., and stirred at this temperature for 20~60 min;

centrifuging the alkalescent first feed liquid in the reaction tank and collecting slag from the alkalescent first feed liquid;

mixing the slag with water to form a second feed liquid, the second feed liquid being heated to 50~90° C. and centrifuged, and collecting slag from the second feed liquid; the same processing is repeated at least twice to obtain purified slag;

the purified slag being mixed with water at a water-slag ratio of 100:40~60, stirred, and subjected to a first enzymolysis and a second enzymolysis by alkali protease and compound protease in sequence to obtain an enzymatic hydrolysate, wherein the compound protease is comprised of papain and neutral protease; and heating the enzymatic hydrolysate to deactivate enzyme, collecting enzymolysis liquid, and post-processing the enzymolysis liquid to obtain the active peptides.

In the present invention, a method of combining alkali-heat treatment with continuous enzymolysis is used to conduct continuous enzymolysis of corn germ proteins and, eventually, to obtain active peptides with biological activity, referred to as "corn antihypertensive active peptide" in the present invention. Enzymolysis products are subjected to appropriate processing and purification as required, to obtain active peptides products in desired form, such as liquid or powder.

According to an embodiment of the present invention, the preparing method above can further comprise the steps of preparing active peptide powders as follows:

the enzymatic hydrolysate after enzyme deactivation is subjected to centrifugation, for example, by controlling rotation speed to be 3000-16000 r/min, and a clear centrifugal liquid is collected, and filtration by a membrane filtration equipment with a pore size of 0.03~0.2 μm, under a pressure of 0.2~0.4 MPa and a temperature of 30~80° C., and then the filtrate is collected;

a concentrated solution with solid content of 20~50% is prepared by concentrating the filtrate under a temperature of 80° C. or less;

activated carbon is added to the concentrated solution for decolorization, and after filtration, the concentrated solution after decolorization is collected; and the concentrated solution after decolorization is subjected to centrifugal spray drying, under conditions of the inlet temperature of 160~180° C. and outlet temperature of 60~90° C., to obtain the active peptide powders.

According to the method of the present invention, firstly the corn germ protein powder is treated with alkali and heat, to remove oil, starch, fiber and other non-protein materials from the raw material, and thus to provide raw material of preparing active peptides by enzymolysis (the substrate for enzymolysis). In a specific embodiment, the mixed feed liquid of corn germ protein powders and water is adjusted to pH 7.5~11, or pH 9~11, heated to 50~90° C., and stirred at this temperature for 20~60 min, for the alkali-heat treatment. In the process, the alkali-heat treatment of corn germ protein powders is conducted at an appropriate concentration, which is beneficial. For example, before the alkali-heat treatment, water is added to the corn germ protein powders at a ratio of water to the corn germ protein powders of 100:6~12 (L:kg) to obtain a feed liquid to be treated. To adjust the feed liquid to alkalescent, any available alkaline substance can be used, preferably the substance can provide alkalescent environment and meanwhile can avoid extra ingredients that may influence the effect of subsequent enzymolysis to be introduced into the feed liquid, for example, conventional alkalis such as sodium carbonate, potassium carbonate, sodium hydroxide, potassium hydroxide and so on can be used, but the present invention is not limited to these alkalis.

The feed liquid after the alkali-heat treatment is subjected to solid-liquid separation and the slag is collected and purified by water treatment. After being purified, the slag is used as the substrate for enzymolysis. The process generally needs to repeat at least once, for example, 2-5 times in general, to remove oil, starch, fiber and other non-protein substances as much as possible.

According to the present invention, the process of continuous enzymolysis includes enzymolysis by alkali protease and enzymolysis by compound protease of the feed liquid after the alkali-heat treatment. The enzymic preparations used can be commercial products, and be used to carry out the enzymolysis under the enzymolysis condition as required by them. For example, appropriate duration of enzymolysis is controlled to conduct the needed enzymolysis at the pH and the temperature appropriate for the enzymic preparations used. In an embodiment, alkali protease is added in the first enzymolysis based on the amount of 2000~5000 units of enzyme (enzyme activity unit, U) per gram of protein in the substrate for enzymolysis. The compound protease used in the second enzymolysis is preferably comprised of papain and neutral protease at an enzyme activity unit (U) radio of 1:1, and is added based on the amount of 1000~2000 units of enzyme (enzyme activity unit, U) per gram of protein in the substrate for enzymolysis. The specific amount can be determined by simple conversions of the enzyme activity of the enzymic preparations purchased.

Enzymic preparation used can be, for example, one or more selected from alkali protease Alcalase 2.4 L, 2709 alkali protease, alkali protease Alcalase 3.0 T, Alcalase (2.4 L FG) and so on; one or more selected from neutral protease Dispase II, Neutrasel 1.5 MG, AS1398 neutral protease, 1398 neutral protease and so on. All the enzymic preparations are commercial available.

In an embodiment, the above enzymolysis process may be as follows: the purified slag is mixed with water at a water-slag ratio of 100:40~60, stirred, adjusted to pH 8~10 and heated to 40~60° C.; the alkali protease is added for the first enzymolysis, which lasts 3-5 h, and then the feed liquid is adjusted to pH 6~8, and the compound protease comprised of papain and neutral protease is added for the second enzymolysis, which lasts 1-3 h at 40~55° C.

The enzymatic hydrolysate after twice enzymolysises is subjected to enzyme deactivation, for example, by heating the enzymatic hydrolysate for a specified time. For example, conditions of enzyme deactivation may be as follows: the enzymatic hydrolysate is heated to 100-13° C., maintained for 10 s-15 min. Appropriate operations of enzyme deactivation can also be determined according to the enzymic preparations used and the degree of enzymolysis, for example, high temperature instantaneous enzyme deactivation may be used.

After enzyme deactivation and necessary separation and concentration treatment, the enzymatic hydrolysate becomes the active peptide product of the present invention, and may be further decolorized and then mixed to obtain a liquid product, or dried to obtain a powder product according to requirements of the final production.

In an embodiment, the enzymatic hydrolysate after enzyme deactivation is decolorized by activated carbon powder in an amount of 3-10% based on the concentrated solution weight, heated to 60~90° C., and stirred at this temperature for 20~40 min A process of industrial production is provided in the present invention. All the devices used are commercially available. Specifications and machine models are selected to match each other according to requirement.

For example, a disk type centrifuge or other relevant devices may be used during centrifugation of the alkalescent feed liquid and separation to prepare purified slag.

A tubular centrifuge or other possible devices may be used during centrifugation of the enzymatic hydrolysate after enzyme deactivation. The clear centrifugal liquid may be further purified by membrane filtration to obtain clear active peptide filtrate, wherein membrane filtration devices with a pore size of 0.03~0.2 μm may be used, such as a microfiltration or ultrafiltration equipment.

A double-effect falling film evaporator can be used to prepare the concentrated solution with a solid content of 20~50% by concentrating the filtrate, under a vapor pressure of 0.1±0.02 MPa, at a temperature of no more than 80° C. such as 40-80° C., and of course, other conventional evaporating devices can also be used.

In a specific embodiment, the corn germ protein powder is mixed with water at a ratio of 100:6~12 (L:kg) of water to corn germ protein powder, adjusted to pH 9~11 and heated to 50~80° C., and stirred at this temperature for 20~60 min. The alkaline feed liquid in the reaction tank is pumped into the disk type centrifuge to separate into the clear liquid and slag. After the collection of the slag, the slag is diluted with water, heated to 50~80° C., stirred and separated. The same processing is repeated three times. Purified slag is mixed with water at a water-slag ratio of 100:40~60, stirred, adjusted to pH 8~10 and heated to 40~60° C. Based on the amount of 2000~5000 units of enzyme(U) per gram of protein, 2.4 L Alcalase is added and the reaction lasts for 3~5 hours. Then, based on the amount of 1000~2000 units of enzyme(U) per gram of protein, papain and Dispase II (1:1) are added at a temperature of 45~55° C., and the enzymolysis lasts for 1~2 hours. Finally, the enzymatic solution was heated to 120° C. and subjected to enzyme deactivation treatment for 10 min.

The corn germ protein enzymatic hydrolysate is centrifuged by tubular centrifuge with a rotating speed of 3000~16000 r/min, such as 12000~16000 r/min. The clear centrifugal liquid is retained and filtered through a microfiltration or ultrafiltration equipment with a pore size of 0.05~0.1 μm, under the conditions of a pressure of 0.2~0.4 MPa, and a temperature of 30~80° C. The filtrate of corn antihypertensive active peptides is evaporated with a double-effect falling film evaporator until the solid content of the concentrated solution is 20~50%, under the conditions of a vapor pressure of 0.1±0.02 MPa, and a temperature of 40~80° C. With the proportion of 5% based on the concentrated solution content, activated carbon powder is added for decolorization and the concentrated solution is heated to 80° C., stirred at this temperature for 20~40 min, and then filtered with a roll nanofiltration membrane. The decolorized concentrated solution of corn antihypertensive active peptides is dried by centrifugal spray dryer to prepare corn antihypertensive active peptide powders, under the conditions of the inlet temperature of 160~180° C., and outlet temperature of 60~90° C., such as 80~90° C.

The present invention provides active peptides (referred to as corn antihypertensive active peptides in the present invention) prepared according to any one of the above mentioned methods. Chemical ingredient analysis of the corn antihypertensive active peptides is used to determine the basic physical and chemical ingredients thereof, and the molecular weight distribution of the corn antihypertensive active peptide ingredients is determined by high-performance liquid chromatography, where the components with molecular weight less than 1000 Da account for no less than 92%, and the content of free amino acids is less than 5%.

The in vitro stability test indicates that, active peptides according to the present invention show good stability in the environment of changing temperature and acidity-alkalinity, as well as in the presence of various enzymic preparations. For example, the corn antihypertensive active peptides have good stability in the temperature range of 30~100° C., a pH range of 3~11, and pepsin digestion, trypsin digestion, pepsin digestion followed by trypsin digestion. Further in vitro test shows that the corn antihypertensive active peptides have good ACE-inhibitory activity in vitro.

By using liquid chromatography separation and mass spectrometry analysis, the peptide fragments in the corn antihypertensive active peptides prepared are separated and structurally identified, where 7 peptide fragments with physiological activities are identified, and where alanine-tyrosine as the characteristic antihypertensive peptide fragments account for no less than 0.6%.

The experiment of spontaneous hypertension rats (SHR) as the model has confirmed that, the active peptides in the present invention have a good antihypertensive effect in vivo, and can be applied to the health care functional food and pharmaceutical fields.

BRIEF DESCRIPTIONS OF THE DRAWINGS

Drawings are briefly described below.

FIG. 1 shows reversed phase chromatograms of corn antihypertensive active peptides under different conditions, where A is a reversed phase chromatogram under different temperature conditions (from top to bottom respectively corresponding to 20° C., 40° C., 60° C., 80° C., and 100° C.); B is a reversed phase chromatogram under different pH conditions (from top to bottom corresponding respectively to a pH of 3, 5, 7, 9, and 11); C is a reversed phase chromatogram under different digestion conditions in vitro (from top to bottom respectively corresponding to the blank control, pepsin digestion, trypsin digestion, and pepsin digestion followed by trypsin digestion).

DETAILED DESCRIPTION

Figure 1:
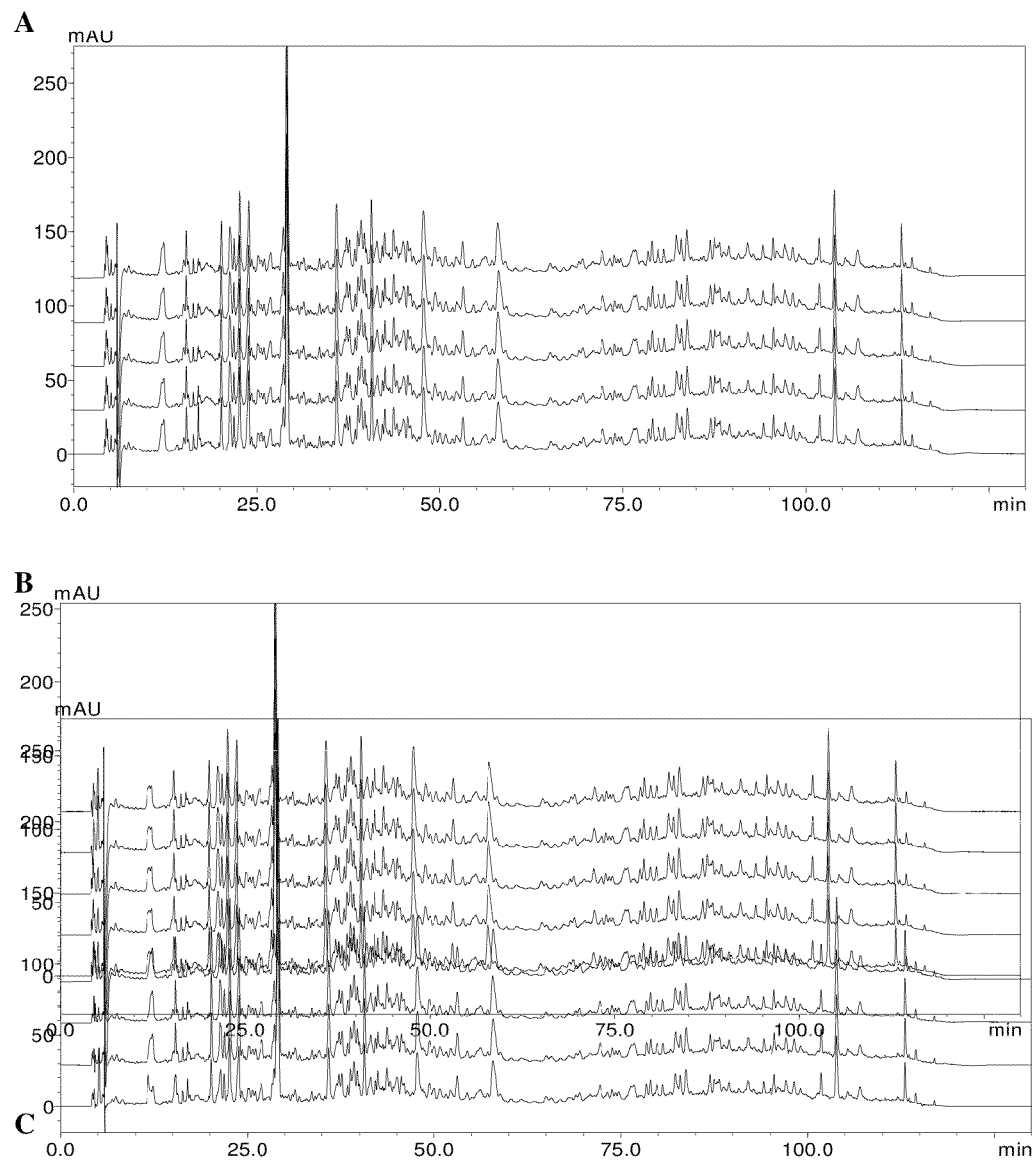

The present invention is further described with reference to the drawings and specific embodiments, which do not limit the scope of the present invention.

Preparation of Corn Antihypertensive Active Peptides

Example 1

600 kg of corn germ protein powders (from Qinhuangdao Lihua Starch Co., Ltd.) was added to a reaction tank I, mixed with water at a ratio of water to the corn germ protein powders of 100:9 (L: kg) to obtain a slurry, pH of the slurry was adjusted to about 10 by addition of food grade sodium hydroxide, and the slurry was heated to about 65° C., and stirred at this temperature for about 40 min. And the alkaline slurry in the reaction tank I was pumped into a disk type centrifuge to separate into clear liquid and slag. The slag collected was added to a reaction tank II, and the clear liquid was discarded. The slag was diluted with water, heated to about 65° C., stirred and separated. The same processing is repeated three times for the separated slag, in order to remove oil, starch, fiber and other non-protein substances, and purified slag was obtained.

The above purified slag was mixed with water at a water-slag ratio of 100:45 and stirred. The mixture solution was adjusted to about pH 8 by addition of food grade sodium hydroxide, and heated to about 50° C. to obtain the substrate for enzymolysis. Based on the amount of 3500 units of enzyme (U) per gram of protein, 2.4 L Alcalase was added into the substrate and the reaction lasted for about 4 hours under this condition for the first enzymolysis. Then, based on the amount of 1500 units of enzyme (U) per gram of protein, papain and Dispase II (1:1) were added (the two enzymic preparations can be added either separately based on the proportion or in the form of complex enzyme preparation prepared in advance), adjusting temperature to 50° C., and the enzymolysis lasted for 1.5 hours for the second enzymolysis. Then, the enzymatic solution was heated to 120° C. and subjected to enzyme deactivation treatment for 10 min.

The above hydrolysate solution after enzyme deactivation was centrifuged by a tubular centrifuge at a rotating speed of 14000 r/min. The clear liquid and slag were separated. And the centrifugal clear liquid was filtered through an ultrafiltration equipment with a pore size of 0.06 μm to intercept macromolecular components to obtain a clear filtrate of the corn antihypertensive active peptides, under the conditions of the pressure of 0.3 MPa and the temperature of 55°. The clear filtrate was evaporated and concentrated with a double-effect falling film evaporator until the solid content of concentrated solution was 40%, under the conditions that vapor pressure was 0.1 MPa and the temperature was 60° C.

With the proportion of 5% by weight of the concentrated solution of the antihypertensive active peptides, activated carbon powder was added for decolorization and the concentrated solution was heated to 80° C., stirred at this temperature for 30 min, and then filtered to obtain a concentrated solution of decolorized corn antihypertensive active peptides. Then, the concentrated solution of the decolorized corn antihypertensive active peptides was dried by centrifugal spray dryer, under the conditions of the inlet temperature of 170° C. and outlet temperature of 85° C. The dried product was collected to obtain 116.25 kg of corn antihypertensive active peptides.

Example 2

600 kg of corn germ protein powders (from Qinhuangdao Lihua Starch Co., Ltd.) was added to a reaction tank I, mixed with water at a ratio of water to the corn germ protein powders of 100:9 (L: kg) to obtain a slurry, the slurry was adjusted to about pH 11 by addition of food grade sodium hydroxide, and heated to about 85° C., and stirred at this temperature for about 30 min. And the alkaline slurry in the reaction tank I was pumped into a disk type centrifuge to separate into clear liquid and slag. The slag collected was added to a reaction tank II, and the clear liquid was discarded. The slag was diluted with water and heated to about 65° C., stirred and separated. The same processing is repeated once for separated slag, in order to remove oil, starch, fiber and other non-protein substances, and the purified slag was obtained.

The above purified slag was mixed with water at a water-slag ratio of 100:60, stirred and adjusted to about pH 9 by addition of food grade sodium hydroxide, and heated to about 50° C.±2° C. to obtain the substrate for enzymolysis. Based on the amount of 0.03 AU (about 3000 U) units of enzyme per gram of protein, alkali protease was added to the substrate for enzymolysis and the reaction lasted for about 4 hours under this condition for the first enzymolysis. Then, based on the amount of 1500 units of enzyme(U) per gram of protein, papain and 1% Neutrase 1.5 MG(1:1) were added (the two enzymic preparations can be added either separately based on the proportion or in form of complex enzyme preparation prepared in advance), and at a temperature of 52° C., the enzymolysis lasted for 2 hours for the second enzymolysis, and an enzymatic solution was obtained. Then, the enzymatic solution was heated to 120° C. and subjected to enzyme deactivation treatment for 5 min.

The above hydrolysate solution after enzyme deactivation was centrifuged by a horizontal screw-conveyor centrifuge at a rotating speed of 3000 r/min. The clear liquid and slag were separated. And the centrifugal clear liquid was retained and was filtered through an ultrafiltration equipment with a pore size of 0.06 μm to intercept macromolecular components to obtain clear filtrate of the corn antihypertensive active peptides, under the conditions of the pressure of 0.3 MPa and the temperature of 55° C. The clear filtrate was evaporated and concentrated with a double-effect falling film evaporator until the solid content of concentrated solution was 40%, under the conditions of the vapor pressure of 0.1 MPa and the temperature of 60° C.

With the proportion of 5% by weight of the concentrated solution of the antihypertensive active peptides, activated carbon powder was added for decolorization and the concentrated solution was heated to 80° C., stirred at this temperature for 30 min, and then filtered to obtain a decolorized concentrated solution of the corn antihypertensive active peptides. Then, the decolorized concentrated solution of the corn antihypertensive active peptides was dried by centrifugal spray dryer, under conditions of the inlet temperature of 170° C. and outlet temperature of 85° C. The dried product was collected to obtain 120.36 kg of corn antihypertensive active peptides.

Composition and Molecular Weight Distribution (MWD) of the Corn Antihypertensive Active Peptides The analysis results of composition of the corn antihypertensive active peptides obtained in example 1 were that: the content of total protein was 89.28%, fat was 0.05%, ash was 5.06%, and moisture was 5.21%. As can be seen, the total protein content of the corn antihypertensive active peptides prepared according to the present invention was over 85%, the product has a high quality.

The relative molecular weight and its distribution of the corn antihypertensive active peptides sample were determined by GEL-HPLC.

The absorption and utilization in human body of dipeptides, tripeptides of the components with molecular weight of 1000 Da or less is extremely high, which have a higher nutritional value and physiological function than free amino acids. Molecular weight 132 Da of the smallest dipeptide (Gly-Gly) and molecular weight of 576 Da of the biggest tripeptide (Trp-Trp-Trp) are used as the boundary value of molecular weight range, and a peak area normalization method is adopted to calculate the molecular weight distribution range of the corn antihypertensive active peptide sample, as shown in Table 1.

From the results of molecular weight distribution, the components with molecular weight less than 1000 Da totally account for 93.05% in the sample. If calculated according to the average molecular weight of 137 Da of amino acids, the components with molecular weight of 1000 Da or less are mostly oligopeptides lower than octapeptide, including some free amino acids. The components with molecular weight of 132 Da-576 Da account for 78.17%, forming most part of the components with molecular weight less than 1000 Da, and are mainly dipeptide, tripeptide and tetrapeptide.

TABLE 1

The molecular weight distribution of the corn antihypertensive active peptides

| Molecular weight range | Start time (min) | End time (min) | Peak area percentage (%, 220 nm) |
|---|---|---|---|
| 10000-1000 | 14.067 | 19.093 | 6.7992 |
| 1000-576 | 19.093 | 20.297 | 10.4944 |
| 576-132 | 20.297 | 23.513 | 78.1669 |
| <132 | 23.513 | 34.171 | 4.3934 |

In Vitro Stability of the Corn Antihypertensive Active Peptides

1. After water bath at 20° C., 40° C., 60° C., 80° C., and 100° C. for 2 h, respectively, the molecular weight distribution of the above corn antihypertensive active peptides sample was determined as shown in Table 2.

It can be seen that after 2 h of water bath at different temperatures, the total content of the components with the molecular weight not more than 1000 Da in the corn antihypertensive active peptides substantially had no change and was maintained at about 93%. The proportion change of components in each molecular weight range was not more than 2%. Reversed phase chromatograms of the corn antihypertensive active peptides at different temperatures were as shown in FIG. 1.A. It can be seen that after 2 hours of water bath at different temperatures, the reversed phase chromatogram of the corn antihypertensive active peptides almost had no change, and the peak number agreed well with the peak time. At the same time, after similarity test, the similarity was about 0.99. That is, from the view of the molecular polarity, there was slight but not obvious change in the composition of the corn antihypertensive active peptides.

TABLE 2

The molecular weight distribution of the corn antihypertensive active peptides at different temperatures

| Temperature (° C.) | Relative molecular weight distribution (%) | | | |
|---|---|---|---|---|
| | 1000-576 Da | 576-132 Da | not more than 132 Da | Total of not more than 1000 Da |
| 20 | 9.61 | 79.59 | 3.39 | 92.59 |
| 40 | 9.45 | 81.07 | 3.31 | 93.82 |
| 60 | 9.59 | 80.68 | 2.98 | 93.26 |
| 80 | 9.63 | 80.80 | 3.04 | 93.48 |
| 100 | 9.41 | 80.53 | 3.66 | 93.59 |

2. After water bath at 37° C. and at a pH of 3, 5, 7, 9, and 11 for 2 h, respectively, the molecular weight distribution of the corn antihypertensive active peptide sample was as shown in Table 3.

Under different pH conditions, after heating for 2 h in 37° C. water bath, the total content of the components with molecular weight not more than 1000 Da in the corn antihypertensive active peptides substantially had no change and was maintained at about 93%. The proportion change of components in each molecular weight range was not more than 1%. A reversed phase chromatograms of the corn antihypertensive active peptides at different pH were as shown in FIG. 1.B. It can be seen that, at different pH, after 2 hours of heating in 37° C. water bath, the reversed phase chromatograms of the corn antihypertensive active peptides almost had no change, and the peak number agreed well with the peak time. At the same time, upon similarity test, the similarity was no less than 0.99. That is, from the view of the molecular polarity, at different pH, there was almost no change in the composition of the corn antihypertensive active peptides.

TABLE 3

The molecular weight distribution of the corn antihypertensive active peptides at different pH conditions

| | Relative molecular weight distribution (%) | | | |
|---|---|---|---|---|
| pH | 1000-576 Da | 576-132 Da | less than 132 Da | total of not more than 1000 Da |
| 3 | 9.55 | 80.46 | 3.11 | 93.11 |
| 5 | 9.54 | 80.16 | 3.26 | 92.97 |
| 7 | 9.57 | 81.01 | 3.01 | 93.59 |
| 9 | 9.58 | 80.41 | 3.11 | 93.11 |
| 11 | 9.58 | 80.65 | 3.03 | 93.26 |

3. After pepsin digestion, trypsin digestion, and pepsin digestion followed by trypsin digestion, respectively, the molecular weight distribution of the corn antihypertensive active peptides was as shown in Table 4 (C: blank control; P: pepsin digestion; T: trypsin digestion; P+T: pepsin digestion followed by trypsin digestion).

In different digestion modes, the total content of components with molecular weight no more than 1000 Da in the corn antihypertensive active peptides was slightly increased, but increased by less than 2%. The proportion of the component in molecular weight range of 1000-576 Da is slightly reduced, but reduced by less than 1%, indicating that there was a very small amount of peptides digested by enzymolysis. Correspondingly, the components in lower molecular weight range were increased slightly, and the increase mainly focused in the region of less than 132 Da, indicating that small portion of the components digested is mainly decomposed into small molecule amino acids.

TABLE 4

The molecular weight distribution of the corn antihypertensive active peptides in different digestion modes

| Digestion mode | Relative molecular weight distribution (%) | | | |
|---|---|---|---|---|
| | 1000-576 Da | 576-132 Da | less than 132 Da | total of not more than 1000 Da |
| C | 9.61 | 79.59 | 3.39 | 92.59 |
| P | 8.88 | 78.02 | 7.44 | 94.34 |
| T | 8.67 | 77.68 | 8.09 | 94.44 |
| P + T | 8.71 | 77.45 | 8.38 | 94.54 |

Reversed phase chromatograms of the corn antihypertensive active peptides after pepsin digestion, trypsin digestion, and pepsin digestion followed by trypsin digestion were as shown in FIG. 1.C. It can be seen that after digestion in different modes, the reversed phase chromatogram of the corn antihypertensive active peptides changed slightly, but the main peak number agreed substantially with the peak time. Compared with the control group, the similarity of each chromatogram calculated by software for similarity calculation was above 0.93. That is, from the view of the molecular polarity, after digested by different enzymes, the composition of the corn antihypertensive active peptides was slightly changed, but the change was small.

4. In vitro ACE inhibitory activity and iconic peptide fragments analysis of the corn antihypertensive active peptides The N-Hippuryl-His-Leu hydrate (HHL) method was used to detect in vitro ACE inhibitory activity of the corn antihypertensive active peptides by HPLC. Specifically, the difference in chromatographic peak area of the hippuric acid in the product before and after adding the antihypertensive active peptides was determined, and the difference can reflect the changes of antihypertensive activity of the antihypertensive active peptides.

ACE inhibition rate was calculated as follows: ACE inhibition rate (%)=(M−N)* 100/N, where M is the peak area of hippuric acid in blank control group (mAU•s); and N is the peak area of hippuric acid in the inhibitor added group (mAU•s).

The ACE inhibition ratio of the corn antihypertensive active peptides solution at different concentrations was as shown in Table 5. After measurement and calculation, the IC50 of the corn antihypertensive active peptides was 1.02 mg/mL (i.e. the concentration of the corn antihypertensive active peptides when the ACE inhibition ratio is 50%), indicating that it has good ACE inhibitory activity in vitro.

TABLE 5

ACE inhibition ratio of the corn antihypertensive active peptide solution at different concentrations

| | Concentration of the corn antihypertensive active peptides, (mg/mL) | | | | |
|---|---|---|---|---|---|
| | 2.0 | 1.5 | 1.0 | 0.5 | 0.25 |
| ACE inhibition ratio (%) | 63.55 | 59.21 | 50.83 | 29.51 | 18.28 |

By using liquid chromatography separation and mass spectrometry analysis, isolation and structure identification of peptides fragments in the corn antihypertensive active peptides were conducted. By comparing the identified structures of 53 peptides fragments with the corn proteomics sequence database, the amino acid sequences of 32 peptide fragments match with the existing fragment sequences in the corn proteomics, indicating that these peptide fragments are generated by the hydrolytic cleavage of the corn protein. By comparing with the active peptide database, it was found that alanine-Tyrosine (Ala-Tyr, AY) with antihypertensive activity is included.

Figure 2:
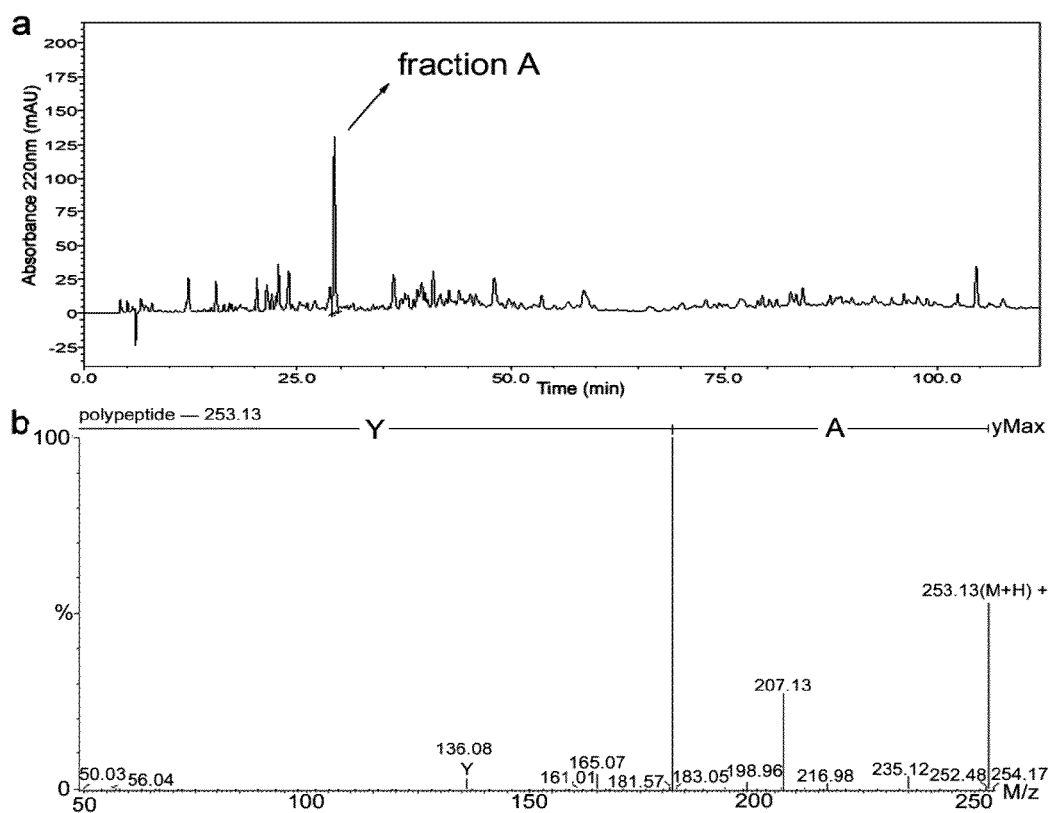
FIG. 2 shows a liquid chromatogram and a mass spectrum of the iconic ingredient AY in the corn antihypertensive active peptides obtained in an embodiment.

YanjunYang et al. found (J. Agric. Food Chem., 2007, 55 (19)) that AY was an antihypertensive peptides, and in vitro antihypertensive activity IC50 thereof was 14.2 μM. The in vivo blood pressure reduction test of SHR indicated that, after oral gavage with AY in 50 mg/kg dose for two hours, the drop of blood pressure of was 9.5 mmHg In the present invention, high-performance liquid chromatography is used to detect AY quantitatively. After being pre-treated, the corn antihypertensive active peptide samples were separated by using a reversed phase C18 filler as the stationary phase according to the difference of molecular polarity of the components in the sample, and detected at the UV absorption wavelength of 220 nm. The external standard method was used to quantify, the chromatogram and its data (FIG. 2) were processed. AY content as calculated was 1.13%.

Different batches of the corn antihypertensive active peptide samples were detected using the same method, and all of them contained no less than 0.6% AY. Therefore AY may be considered as the characteristic component in the corn antihypertensive active peptides of the invention.

5. The antihypertensive effect of the corn antihypertensive active peptides on spontaneous hypertension rat Spontaneous hypertension rats were used as model animals: SPF male SHR rats, 10-11 weeks old, 240-280 g, and systolic pressure>180 mmHg, provided by Department of Laboratory Animal Science of Peking University Health Science Center (laboratory animal use license number: SCXK (Beijing)2006-0025; laboratory animal production license number: SCXK(Beijing)2006-0008). The corn antihypertensive active peptides were gavaged with different doses (0.45, 1.35, and 4.05 g/kg.bw). The blank control group was gavaged with the same volume of distilled water, and the positive control group was gavaged with 10 mg/kg.bw captopril. After 8 weeks of continuous gavage, the body weight, heart/body weight ratio, and heart rate of rats in each group had no significant change (P>0.05).

During the tests, the blood pressures of the control group rats always were around 200 mmHg, and increased slightly over the period of gavage time, but the difference was not significant (P>0.05). The blood pressures of the low-dose group rats (0.45 g/kg.bw) gradually decreased over the period of gavage time. Blood pressure in the sixth week was significantly different (P<0.05), compared with the blank control group, and the significant difference was maintained in the seventh week and the eighth weeks (P<0.05), with blood pressure decreasing by 15.6%. The blood pressures of the middle-dose group rats (1.35 g/kg.bw) decreased slowly over the period of gavage time, until the eighth week, the blood pressure compared to the blank control group was significant different (P<0.05), with blood pressure decreasing by 10.3%. The blood pressures of the high-dose group rats (4.05 g/kg.bw) had a slight decline in 8 weeks of gavage, but compared with the blank control group, the difference is not significant (P>0.05) (Table 6).

Figure 3:
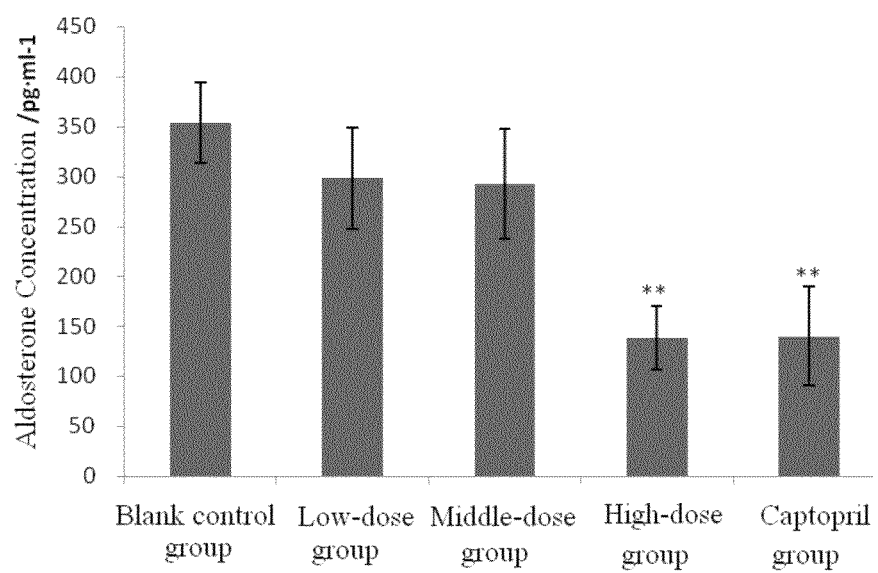
FIG. 3 shows an effect of the corn antihypertensive active peptides obtained in an embodiment on aldosterone concentration in spontaneous hypertension rat serum, wherein n=8, ** indicates a significant difference compared with the blank control group, and $P<0.01$.

Serum aldosterone concentrations of the high-dose group and the captopril group are significantly lower than the control group (P<0.01, FIG. 3). The test results showed that the corn antihypertensive active peptides of the present invention have a significant anti-hypertension effect, and can be used to develop the original ingredients of anti-hypertension drugs and functional foods.

TABLE 6

The antihypertensive effect of the corn antihypertensive active peptides on spontaneous hypertension rats

| Group | 0w | 1w | 2w | 3w | 4w | 5w | 6w | 7w | 8w |
|---|---|---|---|---|---|---|---|---|---|
| Blank control group | 197 ± 15 | 198 ± 22 | 202 ± 15 | 199 ± 10 | 205 ± 16 | 203 ± 9 | 202 ± 10 | 204 ± 11 | 206 ± 13 |
| Low-dose group | 199 ± 14 | 196 ± 12 | 191 ± 10 | 190 ± 17 | 185 ± 14 | 178 ± 18 | 172 ± 9* | 169 ± 14* | 168 ± 10* |
| Middle-dose group | 195 ± 16 | 192 ± 21 | 190 ± 14 | 186 ± 13 | 186 ± 16 | 183 ± 8 | 180 ± 11 | 177 ± 13 | 175 ± 12* |

TABLE 6-continued

The antihypertensive effect of the corn antihypertensive active peptides on spontaneous hypertension rats

| Group | 0w | 1w | 2w | 3w | 4w | 5w | 6w | 7w | 8w |
|---|---|---|---|---|---|---|---|---|---|
| Higher-dose group | 198 ± 12 | 196 ± 17 | 194 ± 17 | 195 ± 23 | 192 ± 16 | 189 ± 16 | 189 ± 13 | 186 ± 14 | 190 ± 16 |
| Captopril group | 193 ± 6 | 184 ± 16 | 177 ± 9 | 174 ± 12 | 170 ± 14* | 168 ± 12* | 164 ± 17** | 162 ± 15** | 161 ± 16** |

Note:
n = 8, unit: mmHg,
*stands for significant difference compared with the blank control group (P < 0.05), and
**stands for significant difference compared with the blank control group (P < 0.01).

The invention claimed is:

1. An active peptide mixture for treating spontaneous hypertension, prepared by enzymolysis of corn germ protein, wherein, in the active peptide mixture, based on the total weight of the active peptide mixture, corn antihypertensive active peptides with molecular weight of less than 1000 Da account for more than 92%, where peptides with molecular weight in the range of 1000-576 Da account for 8.67-9.63%, peptides with molecular weight in the range of 576-132 Da account for 77.45-81.07%, and peptides with molecular weight of less than 132 Da account for 2.98-8.38%, and the content of free amino acids is less than 5%, wherein the active peptide mixture contains at least 0.6% alanine-tyrosine (Ala-Tyr, AY) dipeptide, the active peptide mixture is prepared from corn germ protein powders by the following steps:

adding the corn germ protein powders to a reaction tank, mixing with water at a ratio of water to the corn germ protein powders of 100:6~12 (L: kg) to form a first feed liquid, and the feed liquid being adjusted to pH 7~11, heated to 50~90° C., and stirred at this temperature for 20~60 min;

centrifuging the alkalescent first feed liquid in the reaction tank and collecting the slag from the alkalescent first feed liquid;

mixing the slag with water to form a second feed liquid, which is heated to 50~90° C. and centrifuged, then collecting the slag from the second feed liquid; then repeating the process at least twice to obtain the purified slag;

mixing the purified slag with water at a water-slag ratio of 100:40~60, then stirring, adjusting to pH 7~9, and heating to 40~60° C.; adding an alkali protease for a first enzymolysis, which requires 3-5 h, and then adding a compound protease comprising papain and neutral protease for a second enzymolysis, which requires 1-3 h at 40~55° C., then a enzymatic hydrolysate is obtained; and heating the enzymatic hydrolysate to 100-130° C., maintaining for 10 s-15 min in order to deactivate enzyme, collecting the enzymolysis liquid;

and then the enzymolysis liquid is subjected to centrifugation by controlling rotation speed to be 3000-16000 r/min, and a clear centrifugal liquid is collected, and filtration by a membrane filtration equipment with a pore size of 0.03~0.2 nm, under a pressure of 0.2~0.4 MPa and a temperature of 30~80° C., and then the filtrate is collected;

a concentrated solution with solid content of 20~50% is prepared by concentrating the filtrate under a temperature of 80° C. or less;

activated carbon is added to the concentrated solution for decolorization, and after filtered, the concentrated solution after decolorization is collected; and the concentrated solution after decolorization is subjected to centrifugal spray drying, under conditions of the inlet temperature of 160~180° C. and outlet temperature of 60~90° C., to obtain the active peptide mixture powders.

2. The active peptide mixture for treating spontaneous hypertension, prepared by enzymolysis of corn germ protein, wherein, in the active peptide mixture, based on the total weight of the active peptide mixture, corn antihypertensive active peptides with molecular weight of less than 1000 Da account for more than 92%, where peptides with molecular weight in the range of 1000-576 Da account for 8.67-9.63%, peptides with molecular weight in the range of 576-132 Da account for 77.45-81.07%, and peptides with molecular weight of less than 132 Da account for 2.98-8.38%, and the content of free amino acids is less than 5%, wherein the active peptide mixture contains at least 0.6% alanine-tyrosine (Ala-Tyr, AY) dipeptide, the active peptide mixture is prepared from corn germ protein powders by the following steps:

adding the corn germ protein powders to a reaction tank, mixing with water at a ratio of water to the corn germ protein powders of 100:6~12 (L: kg) to form a first feed liquid, and the feed liquid being adjusted to pH 7~11, heated to 50~90° C., and stirred at this temperature for 20~60 min;

centrifuging the alkalescent first feed liquid in the reaction tank and collecting the slag from the alkalescent first feed liquid;

mixing the slag with water to form a second feed liquid, which is heated to 50~90° C. and centrifuged, then collecting the slag from the second feed liquid; then repeating the process at least twice to obtain the purified slag;

mixing the purified slag with water at a water-slag ratio of 100:40~60, then stirring, adjusting to pH 8~10, and heating to 40~60° C.; based on the amount of 2000~5000 units of enzyme per gram of protein in the substrate for enzymolysis, adding 2.4 L Alcalase for the first enzymolysis, which requires 3-5 h, and then, adding the compound protease comprising papain and Dispase II at an enzyme activity ratio of 1:1 for the second enzymolysis, which requires 1-3 h at 40~55° C., then the enzymatic hydrolysate is obtained; and heating the enzymatic hydrolysate to 100-130° C., maintaining for 10 s-15 min to deactivate enzyme, collecting the enzymolysis liquid;

and then the enzymolysis liquid is subjected to centrifugation by controlling rotation speed to be 3000-16000 r/min, and a clear centrifugal liquid is collected, and filtration by a membrane filtration equipment with a pore size of 0.03~0.2 μm, under a pressure of 0.2~0.4 MPa and a temperature of 30~80° C., and then the filtrate is collected;

a concentrated solution with solid content of 20~50% is prepared by concentrating the filtrate under a temperature of 80° C. or less;

activated carbon is added to the concentrated solution for decolorization, and after filtered, the concentrated solution after decolorization is collected; and the concentrated solution after decolorization is subjected to centrifugal spray drying, under conditions of the inlet temperature of 160~180° C. and outlet temperature of 60~90° C., to obtain the active peptide mixture powders.

3. An active peptide mixture for treating spontaneous hypertension according to claim 1, wherein the content of free amino acids is not zero.

4. An active peptide mixture for treating spontaneous hypertension according to claim 2, wherein the content of free amino acids is not zero.

* * * * *